United States Patent [19]
Swor et al.

[11] Patent Number: 6,148,297
[45] Date of Patent: Nov. 14, 2000

[54] HEALTH CARE INFORMATION AND DATA TRACKING SYSTEM AND METHOD

[75] Inventors: G. Michael Swor; Donald K. Lawrence, both of Sarasota, Fla.

[73] Assignee: Surgical Safety Products, Inc., Sarasota, Fla.

[21] Appl. No.: 09/088,329

[22] Filed: Jun. 1, 1998

[51] Int. Cl.[7] .................................................. G06F 17/30
[52] U.S. Cl. ................................. 707/3; 707/2; 707/10; 705/2; 705/4; 709/203; 709/219
[58] Field of Search ......................... 707/2, 3, 10; 705/2, 705/4; 709/203, 219

[56] References Cited

U.S. PATENT DOCUMENTS

| | | | |
|---|---|---|---|
| 3,970,996 | 7/1976 | Yasaka et al. | 340/172.5 |
| 4,130,881 | 12/1978 | Haessler et al. | 364/900 |
| 4,347,568 | 8/1982 | Giguere et al. | 364/300 |
| 4,803,039 | 2/1989 | Impink, Jr. et al. | 376/216 |
| 5,088,037 | 2/1992 | Battaglia | 364/413 |
| 5,291,399 | 3/1994 | Chaco | 364/413.02 |
| 5,517,405 | 5/1996 | McAndrew et al. | 364/401 |
| 5,530,857 | 6/1996 | Gimza | 707/10 |
| 5,537,315 | 7/1996 | Mitcham | 395/408 |
| 5,572,421 | 11/1996 | Altman et al. | 395/203 |
| 5,583,758 | 12/1996 | McIlroy et al. | 395/202 |
| 5,586,024 | 12/1996 | Shaibani | 364/413.02 |
| 5,619,991 | 4/1997 | Sloane | 128/630 |
| 5,675,744 | 10/1997 | Tsujii | 395/203 |
| 5,752,054 | 5/1998 | Garber et al. | 707/506 |
| 5,879,163 | 3/1999 | Browne et al. | 434/236 |
| 5,884,275 | 3/1999 | Peterson et al. | 705/7 |

FOREIGN PATENT DOCUMENTS

| | | |
|---|---|---|
| 0 764 911 A1 | 3/1997 | European Pat. Off. . |
| WO 96/13790 | 5/1996 | WIPO . |
| WO 97/43728 | 11/1997 | WIPO . |
| WO 98/20439 | 5/1998 | WIPO . |

*Primary Examiner*—Jean R. Homere
*Attorney, Agent, or Firm*—Allen, Dyer, Doppelt, Milbrath & Gilchrist, P.A.

[57] ABSTRACT

An interactive system and method includes at least two subsystems: one for providing exposure and incident information to a healthcare worker and another for collecting exposure and incident data at a healthcare facility in a confidential manner. The system includes input/output devices and a processor for accessing and displaying information on a desired healthcare topic and for collecting, via a series of interactive screens, accident data for subsequent collation within a facility and/or on a multifacility scale, such as for regulatory compliance. Data collection is preferably done in a confidential manner, and a report is generated that includes a risk assessment and recommended followup procedures. The input/output devices are preferably located in close proximity to an area having a relatively high likelihood of exposures or incidents, for permitting the user ready access to desired information.

33 Claims, 11 Drawing Sheets

FIG. 6A1.

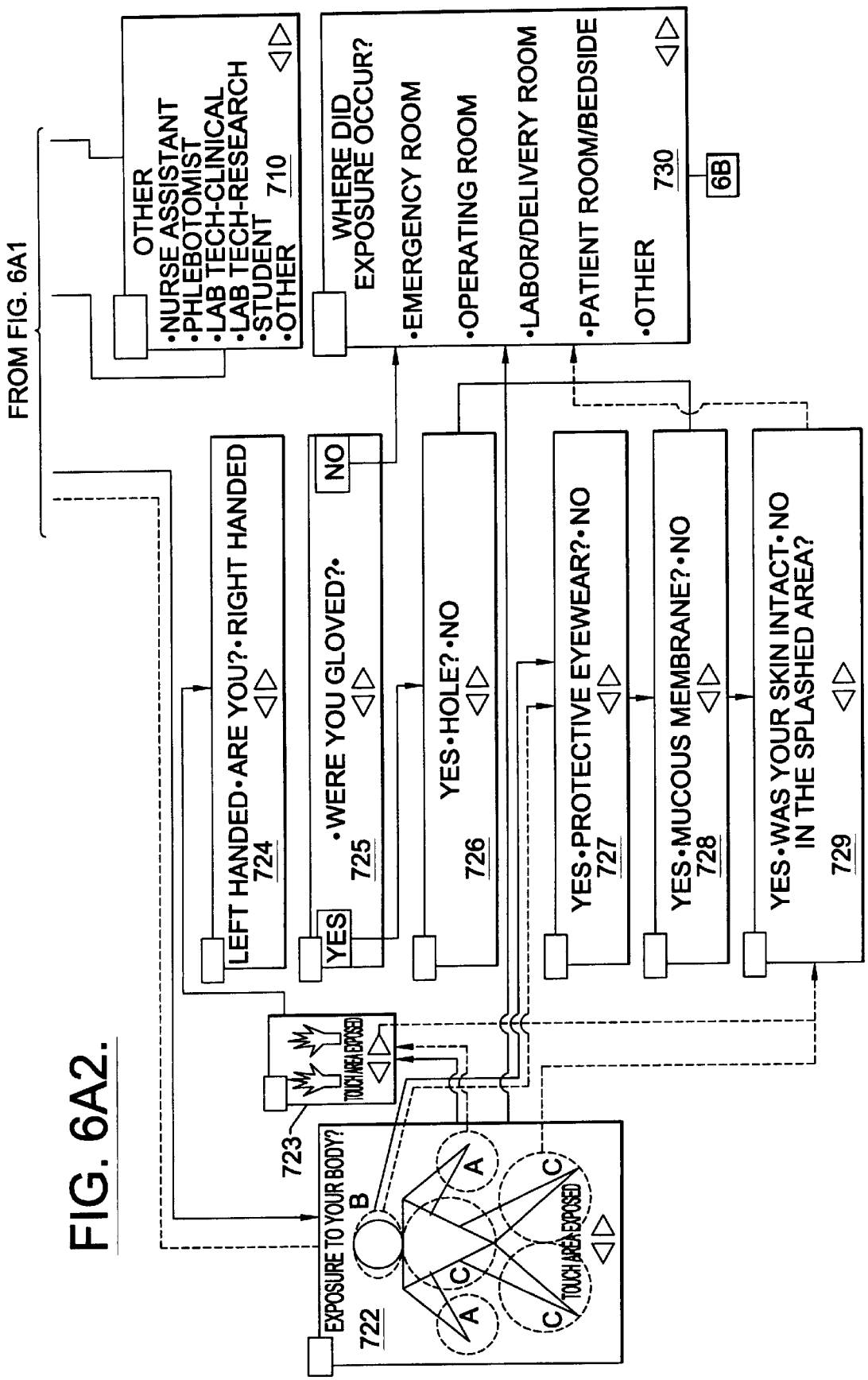

HEALTH CARE INFORMATION AND DATA TRACKING SYSTEM AND METHOD

BACKGROUND OF THE INVENTION

1. Field of the Invention

The present invention relates to systems and methods for providing and managing health care data, and, more particularly, for providing information to health care workers, receiving data regarding occupational safety, and interacting with a remote agency.

2. Description of Related Art

Health information systems have been the subject of considerable development efforts. Increasing demands placed by regulatory agencies and the organizations that provide health care for a patient require extensive information dissemination, record-keeping, and report generation, time-intensive but non-revenue-generating activities.

In particular, occupational incidents such as exposures to blood and other bodily fluids through needle sticks or splashes/splatters are required to be reported to the Occupational Safety and Health Administration (OSHA); however, it is estimated that nine out of ten are not (J. Jagger and M. Balon, *Adv. Expos. Prevention* 1, 1–8, 1995). Reasons for such underreporting include a lack of information about reportable incidents, a fear of the consequences or reporting, embarrassment over the incident, and time required to complete a report.

The importance of providing and collecting timely and accurate information is obvious. Not only will the healthcare worker receive prompt and appropriate treatment; he/she will also have better information regarding the incident and a clearly defined course of followup. It is known that an important technique in preventing such accidents is tracking and analyzing the causes and circumstances surrounding the exposure.

At present, however, there is no known system that integrates information providing and data collecting functions for occupational safety breaches and for furnishing training information on new technologies, devices, and procedures. Further, there is no known interrelated system that links multiple locations within a healthcare site with a regulatory agency for receiving up-to-date training information and to transmit exposure incident data.

Among related art are the medical collecting apparatus of Yasaka et al. (U.S. Pat. No. 3,970,996) and Haessler et al. (U.S. Pat. No. 4,130,881) for receiving and storing data related to individual patients.

The surveillance system of Giguere et al. (U.S. Pat. No. 4,347,568) tracks employee work locations and the past or present location of potentially hazardous substances. Battaglia (U.S. Pat. No. 5,088,037) discloses a portable unit for displaying sequentially standard rescue steps in an emergency.

The distributed data processing network of Chaco (U.S. Pat. No. 5,291,399) is disclosed as usable in a hospital setting. McAndrew et al. (U.S. Pat. No. 5,517,405) describe an expert system for managing health care. The kiosk taught by Mitcham (U.S. Pat. No. 5,537,315) collects user data and issues insurance. Altman et al. (U.S. Pat. No. 5,572,421) disclose a device into which data are to be entered by a patient in response to a questionnaire. The system described by McIlroy et al. (U.S. Pat. No. 5,583,758) receives patient data and assists in the clinical decision process and health care management. Sloane (U.S. Pat. No. 5,619,991) teaches a system for medical diagnosis and/or treatment via a data communications network. The medical workstation described by Tsujii (U.S. Pat. No. 5,675,744) permits sharing data among facilities.

SUMMARY OF THE INVENTION

It is therefore an object of the present invention to provide a health care information system and method for integrating an information providing medium with a data collection network for assisting in handling and reporting occupational accidents.

It is another object to provide such a system and method that is adapted to receive updated training information from a remote location.

It is an additional object to provide such a system and method that is adapted to electronically transmit exposure data to a remote location.

It is a further object to provide such a system and method that provides confidentiality to the user.

It is yet a further object to provide such a system and method that is easy to use by non-technologically oriented workers.

It is yet another object to provide such a system and method that is easily accessible from healthcare facility locations having a relatively high likelihood of exposure incidents and/or other accidents.

It is yet an additional object to provide such a system and method that permit usage at a location remote from a "home base."

Another object is to provide such a system and method for providing a risk analysis to a healthcare worker onsite and on demand.

An additional object is to provide such a system and method for reducing occurrences of incidents and exposures in a healthcare facility.

These objects and others are attained by the present invention, a healthcare information providing and collection system and method for addressing incidents and exposures. The system preferably comprises at least one, and preferably both, of two interrelated subsystems, each having a component resident within a processor housed at or portable to a healthcare facility site. Such sites may include, but are not intended to be limited to, hospitals, clinics, and medical or dental offices. In addition, an embodiment is contemplated for portability by such users as emergency or home-care workers.

The healthcare worker should preferably have easy access to the system from high-risk areas within the facility. By "high-risk areas" is meant regions having a relatively high probability of accidents such as, but not limited to, exposure to pathogens, contact with bodily fluids, and/or sharps injuries. These areas include emergency rooms, operating rooms, dental offices, emergency clinics, and accident sites.

In a particular embodiment the facility, typically a larger facility such as a hospital or clinic, contains a plurality of means for accessing the system of the present invention. Such access means, referred to herein as "kiosks," are typically linked via, for example, a local-area network (intranet), to a central processor. In smaller settings there may be just one access means for serving the healthcare workers located there. In the remote-use embodiment the access means may comprise, for example, a portable computer or hand-held device.

The first subsystem, referred to as an information system, comprises means for performing a plurality of in-house information providing functions. Such information to be provided may include, but is not intended to be limited to, exposure and incident procedures, safety education, product information and usage training, safety news and events, and policies. The information system also comprises input/output (I/O) means for interacting with a user, such as, but not limited to, a touch screen and/or keyboard with a pointing device, and for displaying requested information, such as a monitor-type screen. Means for outputting a hard or electronic copy of selected information can also be included, such as a printer and/or disc drive.

The second subsystem, a data collection system, comprises a means for electronically accumulating data from the user, such as incident or exposure data. In one embodiment, the data collection system further comprises means for communicating with a remote site, such as a central computer within the facility, which permits electronically managing the collected data from throughout the facility, substantially without human intervention. Preferably the user is able to operate anonymously, with a code name or number given for further interaction. In a further embodiment, electronic link means are also provided for achieving data transfer with a remote facility, such as a regulatory organization. This feature permits, for example, reporting accidents, including exposures and incidents, automatically, eliminating excess paperwork and the involvement of a party other than the user, thus permitting confidentiality.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–6D. The interactive healthcare safety system comprises two interrelated subsystems, an information system and a data collection system, which alone and in combination can be used to materially enhance the safety education level of the healthcare staff and the occupational safety of the facility. Herein the word facility will be used to indicate a unit operating under common processor control for the purposes of the present invention and typically will mean a building or complex of buildings such as a hospital, clinic, or data collection facility. The word site will mean a location within the facility, typically the location of at least an I/O portion of the invention. The word area will mean a region within the facility such as an operating room or emergency room.

System Hardware Configuration

Figure 1:
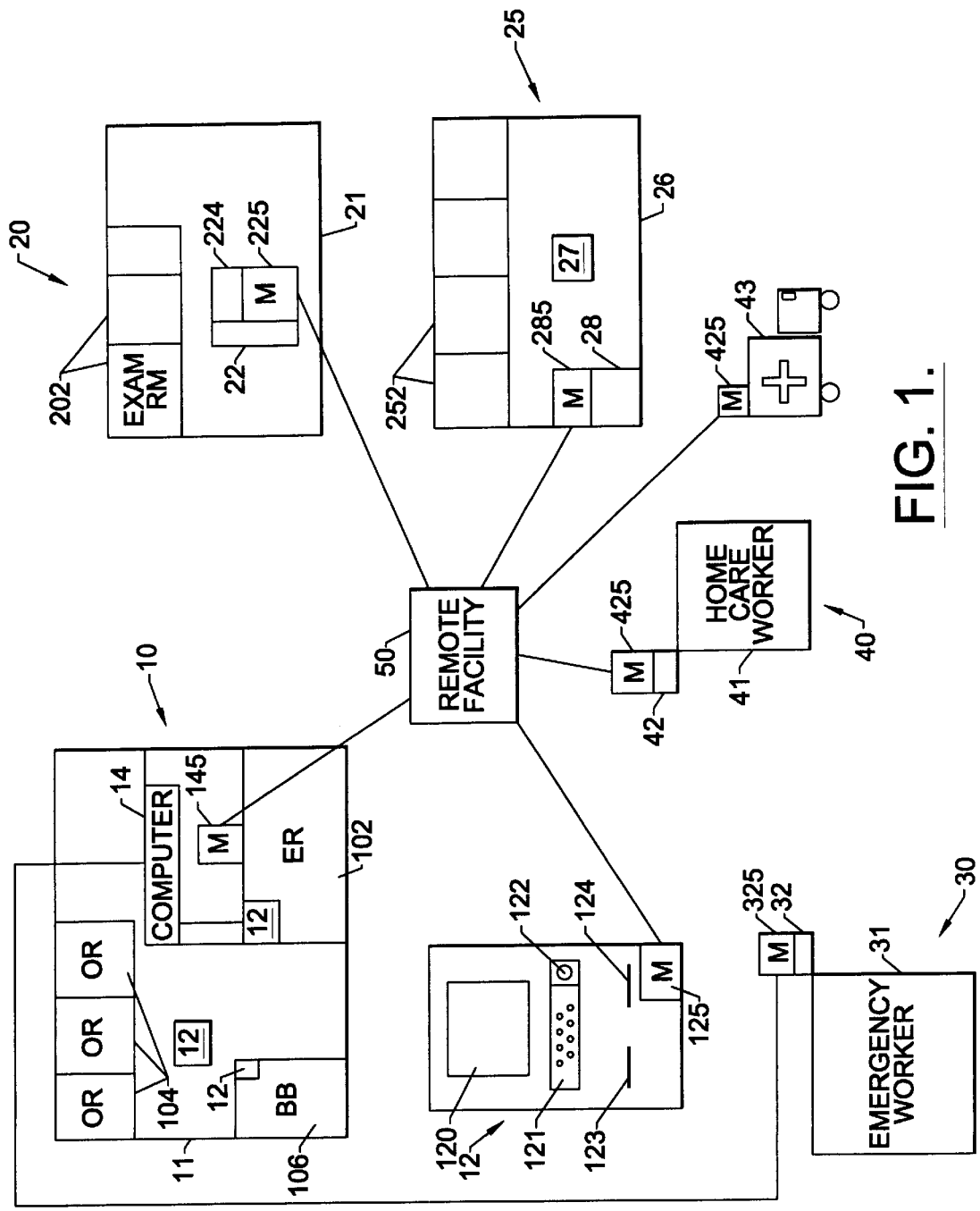
FIG. 1 is a schematic for the information providing and data collection system of the present invention.

There are several embodiments for the hardware configuration of the present invention, as illustrated in FIG. 1. In all cases the system comprises a processor in electronic communication with an input and an output device. Also in each embodiment the processor preferably comprises means for communication with a remote facility 50 such as a regulatory agency or central data collection facility.

In a first embodiment the system 10 comprises a plurality of terminals 12, called "kiosks," each having I/O means, and a central processor 14 networked to the kiosks 12. The I/O means can include any or all of a touch-screen or video monitor 120; a keyboard 121 and/or pointing device 122; a printer 123; a disc drive 124; a modem 125 for communication with the remote facility 50; and any other devices such as are known in the art. The central processor 14 has a modem 145 or direct link for accessing the remote facility 50. This embodiment is contemplated for use in large facilities 11 such as hospitals, with a kiosk 12 placed for easy access from each high-risk area, such as emergency 102 and operating 104 rooms and a blood bank 106.

In a second embodiment the system 20 comprises a unitary kiosk 22 located within the facility 21 comprising the processor 224 and the I/O means 220 (e.g., video monitor, keyboard, pointing device, printer, disc drive) in electronic communication with each other. Alternatively the system 25 can comprise a unitary kiosk 27 networked to a server 28 that also carries out other duties for the facility 26, such as billing and scheduling. These embodiments 20,25 are useful for small healthcare facilities 21,26 such as clinics and dental offices having a limited high-risk area 202,252. The kiosk 22,27 is preferably placed for rapid and easy access from the high-risk area 202,252, which can comprise, for example, examining rooms or dental chairs. In both cases 20,25 the processor/server 224/28 also preferably contains means for accessing the remote facility 50, typically, but not limited to, a modem 225/285.

The third embodiment of the system 30 comprises a substantially portable unit 32, such as a portable computer, a handheld processor. or a personal digital assistant. Preferably the unit 32 contains means such as a modem 325 for communicating with a central processor 14 such as might be located at a "home base," shown in FIG. 1 as a hospital 11, but may also include other facilities such as a fire station. In an alternate embodiment 40 the unit 42 contains means such as a modem 425 for direct communication with the remote facility 50. These embodiments 30,40 are useful, for example, for emergency workers 31 deployed from their "home base," for home-care workers such as visiting nurses or hospice workers 41, and for use in mobile blood-collection vehicles 43.

In all embodiments of the system it is preferred that the I/O means be placed for ready access from a high-risk area as defined above and should preferably be user-friendly to encourage usage by those with limited computer skills. That is, visuals should be highly descriptive and suggestive, and the steps to receive information and enter data should be clearly outlined and easily understood, especially as the user may be under considerable stress if an incident or exposure has occurred.

It may be readily contemplated by one of skill in the art that any number of combinations and subcombinations of the above-recited elements and other equivalent elements can be configured for any particular size or type of facility, and the embodiments given above are not intended to limit the scope of the invention.

Information Subsystem

Figure 2:
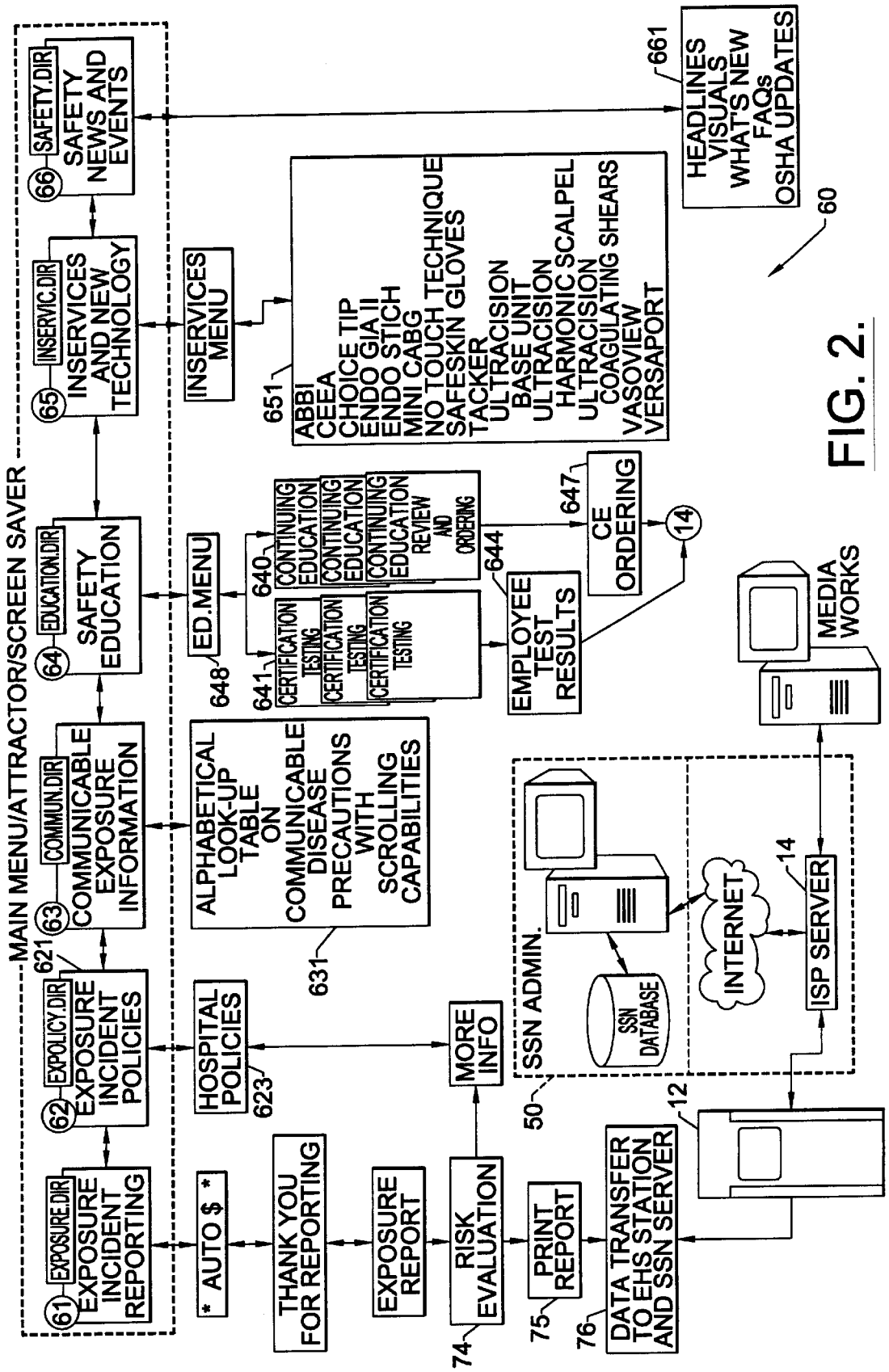
FIG. 2 is a flowchart of exemplary user-system interactions for reporting an exposure or incident and for obtaining policy, safety, training, and news and events information.

The elements of the information subsystem 60 of the present invention are illustrated in FIG. 2. This discussion will address a kiosk 12 such as described for the first embodiment of the system 10, although this is not intended as a limitation, as any of the systems outlined are usable to access the information subsystem.

Using any of the I/O devices as outlined above, the healthcare worker selects (e.g., by pressing a touch-screen icon), typically from a Windows®-type menu, from a plurality of information topics.

Figure 3:
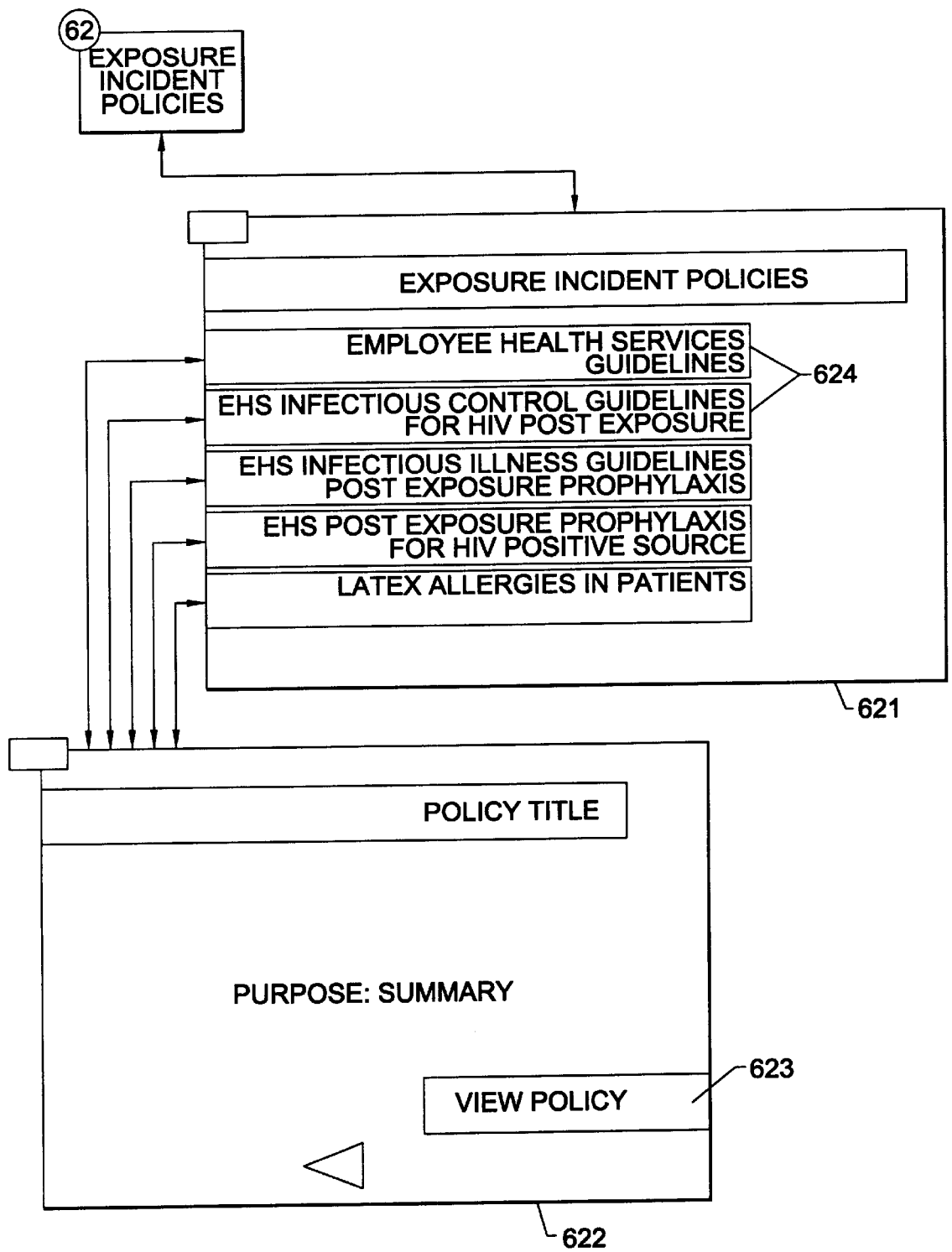
FIG. 3 is a flowchart illustrating the exposure incident policy section of the information subsystem.

A first topic comprises exposure and incident policies 62 (FIG. 3). An exemplary opening window 621 comprises a menu of possible occurrences 624, a choice of one of which brings up another screen 622 displaying a summary of the policy for the chosen occurrence. From this screen the user can then choose to view the full policy (block 623).

A second topic comprises communicable disease information (block 63). In an exemplary embodiment an opening window comprises an alphabetical lookup table 631 with scrolling capabilities. Selecting a particular disease causes the system 60 to display communicable disease precautions. Such material can be downloaded, for example, from a remote site 50 such as an OSHA or NIH website or database into the central processor 14, at predetermined intervals. This is true for all the following topics, and will not be repeated below.

Figure 4A:
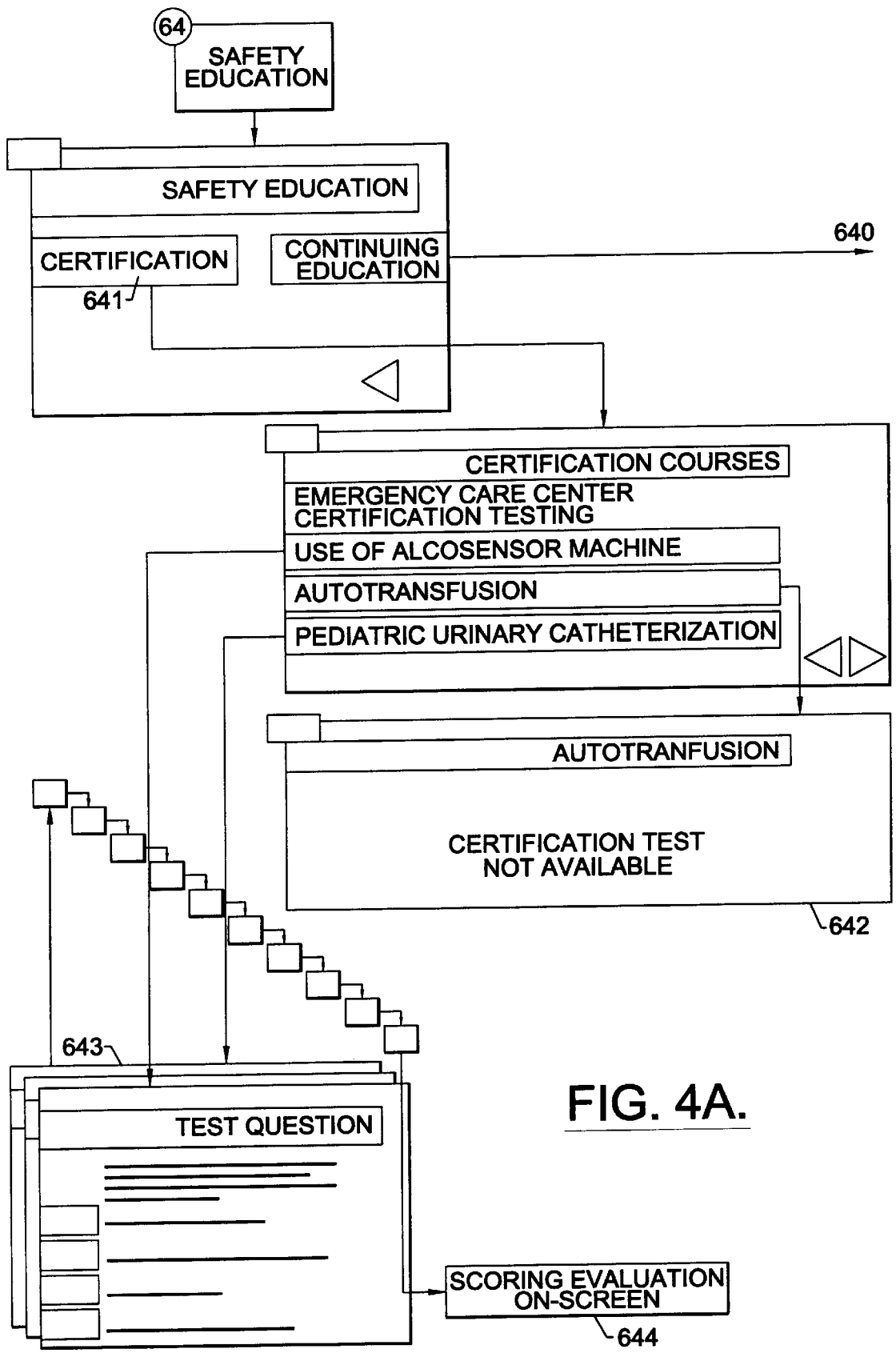
FIG. 4A is a flowchart illustrating the certification portion of the safety education subsystem.
Figure 4B:
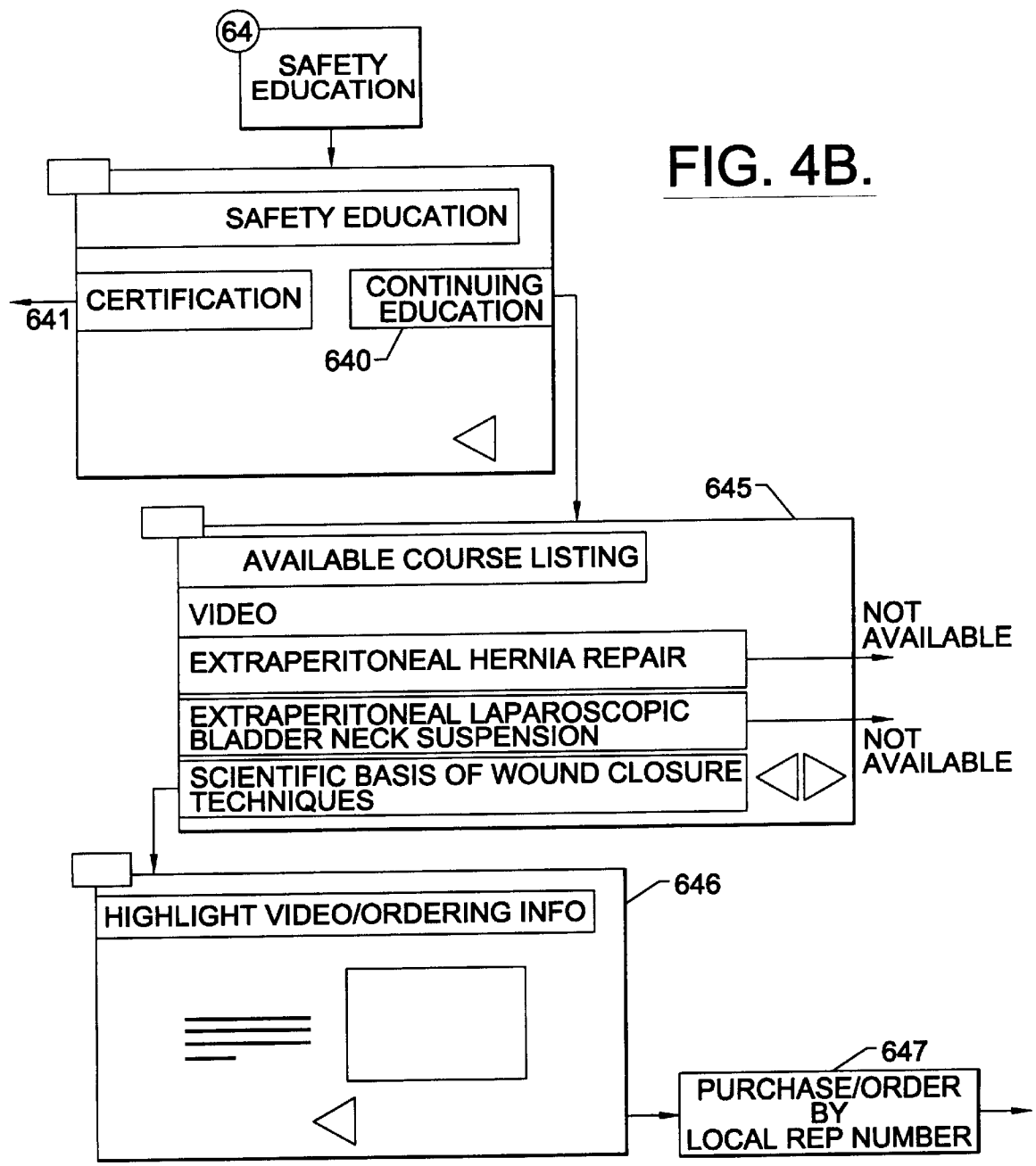
FIG. 4B is a flowchart illustrating the continuing education portion of the safety education subsystem.

A third topic comprises safety education (block 64), which presents the user with a choice 648 between certification courses 640 and tests 641 (FIG. 4A) and continuing education (FIG. 4B). For the former, if a certification test is not available in a selected subject area, the user is so informed 642. When the user has taken a test 643, which is done interactively using methods well known in the art, the answers are routed to a scoring module 644, which displays the test results to the user and transmits them to the central processor 14. If the score is satisfactory, the scoring module 644 also grants certification on the selected subject area.

For the choice of continuing education, an available course listing 645 is presented to the user, from which in turn is selected a topic. Next the user is offered course materials 646, such as a video or book, a request for which is routed 647 via the processor 14 to a vendor or to the hospital library. Alternatively, material could be output directly to the user, such as on disc or paper; or the material could be displayed via video tape to the user at the kiosk 12.

Figure 5:
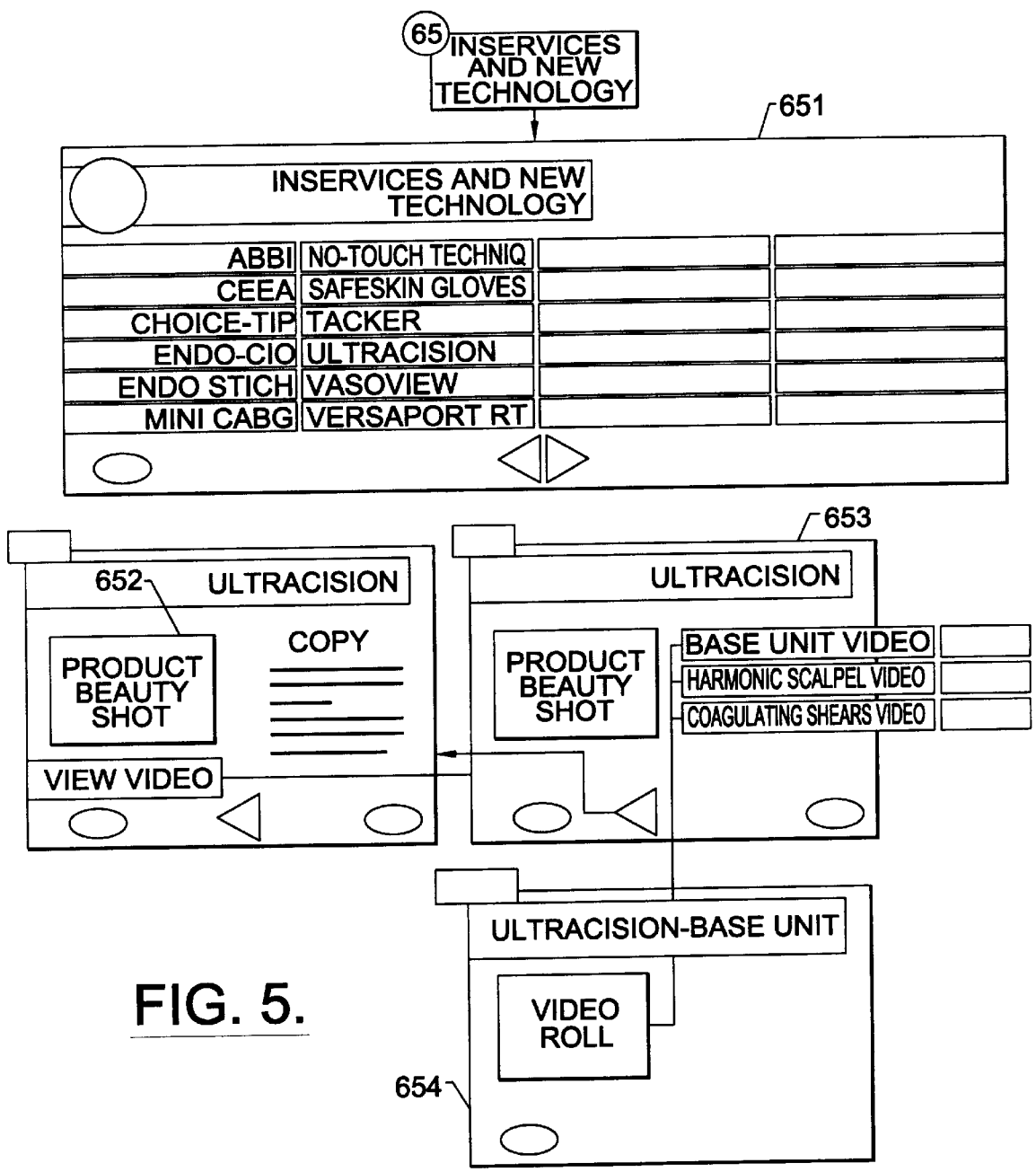
FIG. 5 is a flowchart illustrating the inservices and new technology information option.

A fourth topic comprises inservices and new technology 65 (FIG. 5). A menu of subject areas 651 permits the user to select, for example, a piece of equipment. The illustrative example of FIG. 5 displays material on "ultracision," including a view of the product 652, a choice of videos on subtopics 653, and a prompt to roll the video 654.

A fifth topic comprises safety news and events 66. Among the material that could be presented 661 are health headlines, visuals, answers to frequently asked questions, and OSHA updates.

Data Collection Subsystem

A general schematic of an exemplary embodiment of the data collection subsystem 61 of the present invention is illustrated on the left-hand side of FIG. 2, with a more detailed schematic in FIGS. 6A–6D. The user who has experienced an accident accesses the subsystem 61 from the main menu via, for example, the elements of the kiosk 12, although this is not intended as a limitation, and one of skill in the art will recognize that the alternate embodiments will be utilized via their respective I/O devices.

Figure 6A:
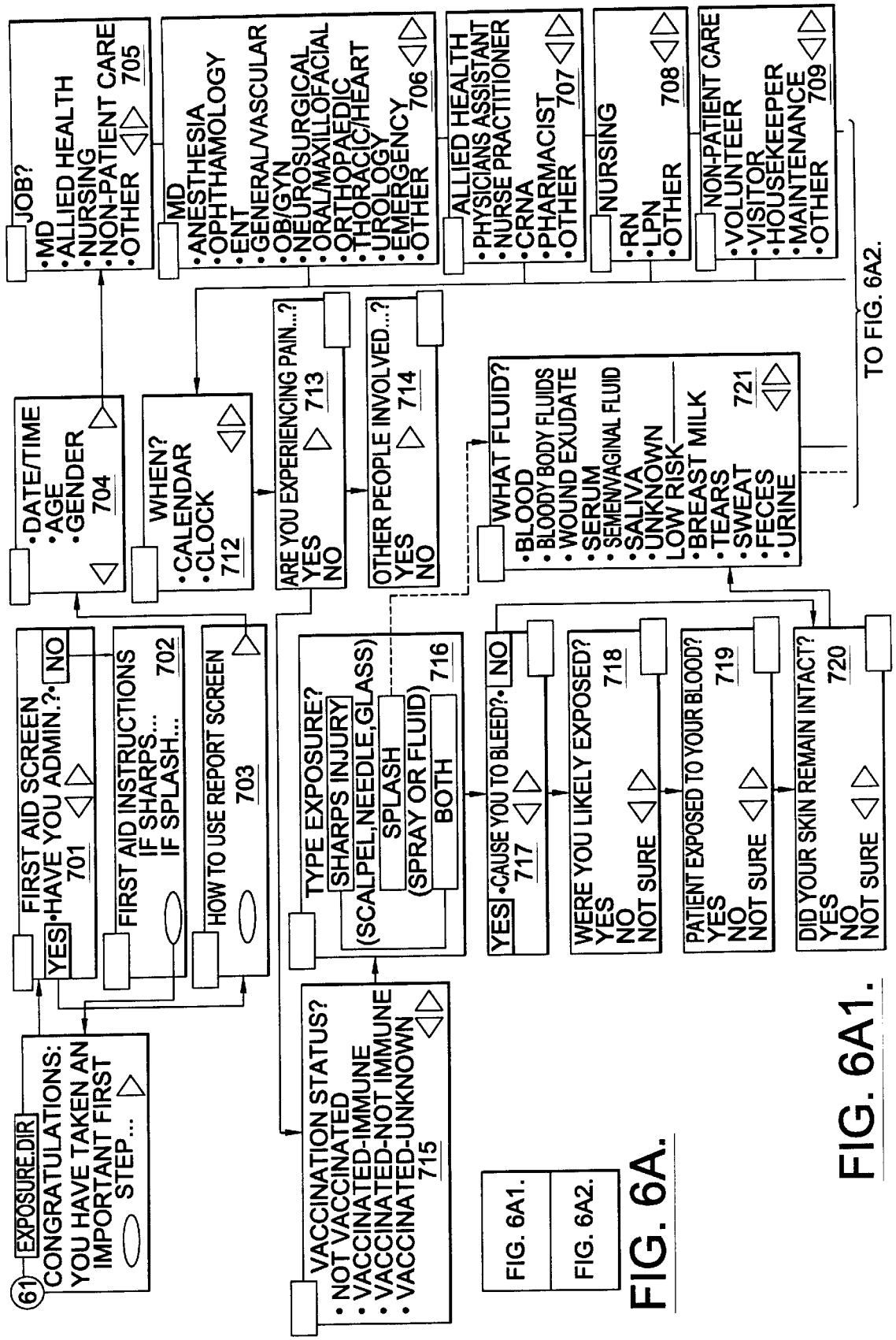
FIGS. 6A–6D comprise a flowchart of exemplary user-system interactions for reporting an exposure incident and receiving a risk assessment.

In a preferred embodiment the user is presented with a series of questions and prompts. As shown in FIG. 6A, first the user is asked whether first aid has been administered (block 701). If not, instructions are given for the appropriate accident (block 702). Next instructions are given for using the Report Screen (block 703), and user data are collected, such as date/time, age, and gender (block 704). The user's position (job) is entered (blocks 705–710), as well as the time of the accident (block 712), whether pain is being experienced (block 713), the involvement of other people (block 714), and vaccination status (block 715). Once the type of exposure is ascertained (block 716), such as sharps or splash, the user is presented with appropriate questions. If sharps, the user is asked if he bled (block 717), is he were exposed (block 718), if the patient was exposed to the user's blood (block 719), and if the user's skin remained intact (block 720). If splash, and after the sharps questions, the type of fluid is ascertained (block 721), as well as the area of the body exposed (blocks 722,723). Further information gather includes handedness (block 724), the use of gloves (block 725) and their integrity (block 726), the use of protective eyewear (block 727) and exposure of mucous membrane (block 728) and the intactness of the skin (block 729).

Figure 6B:
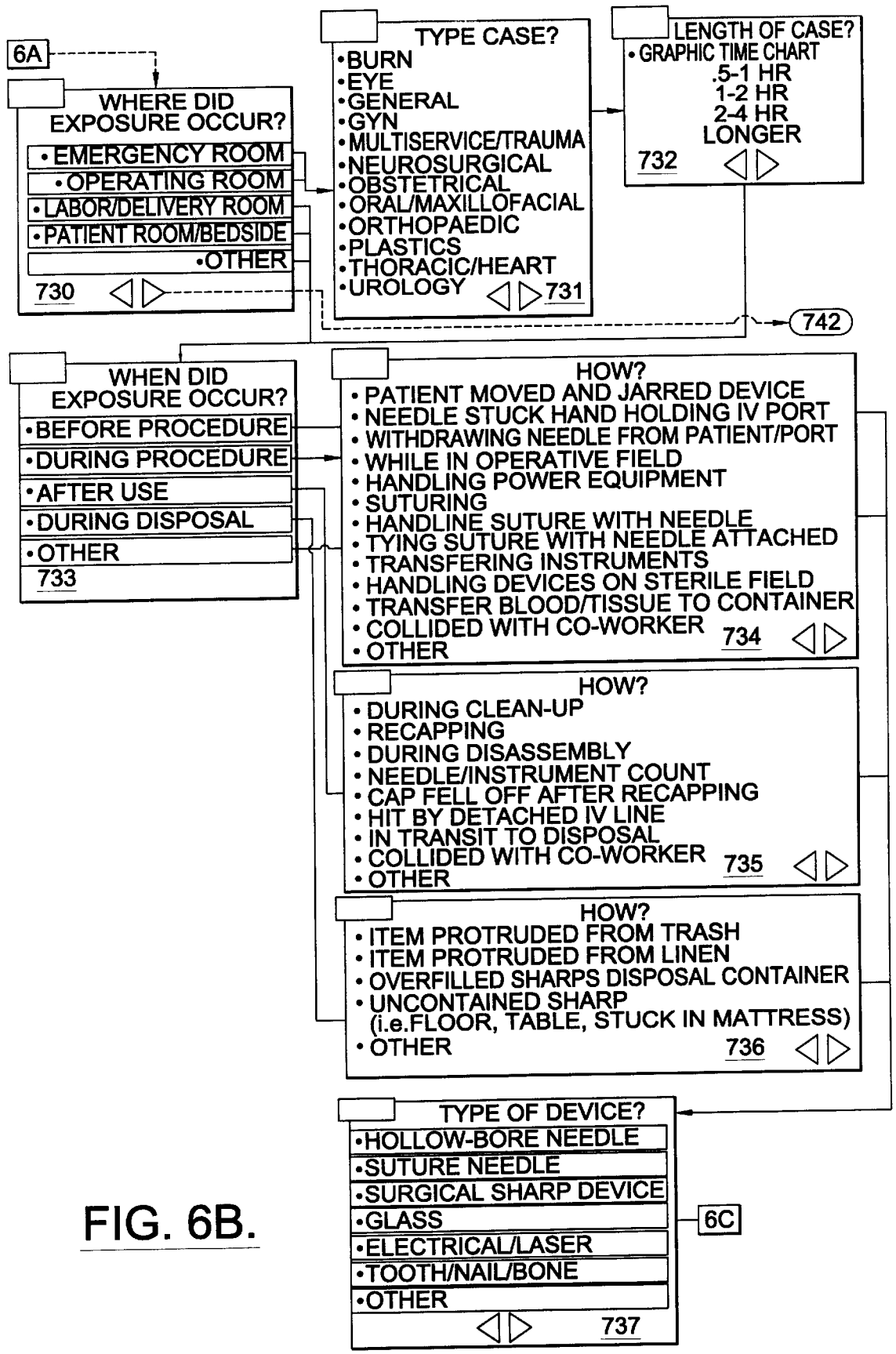
Figure 6C:
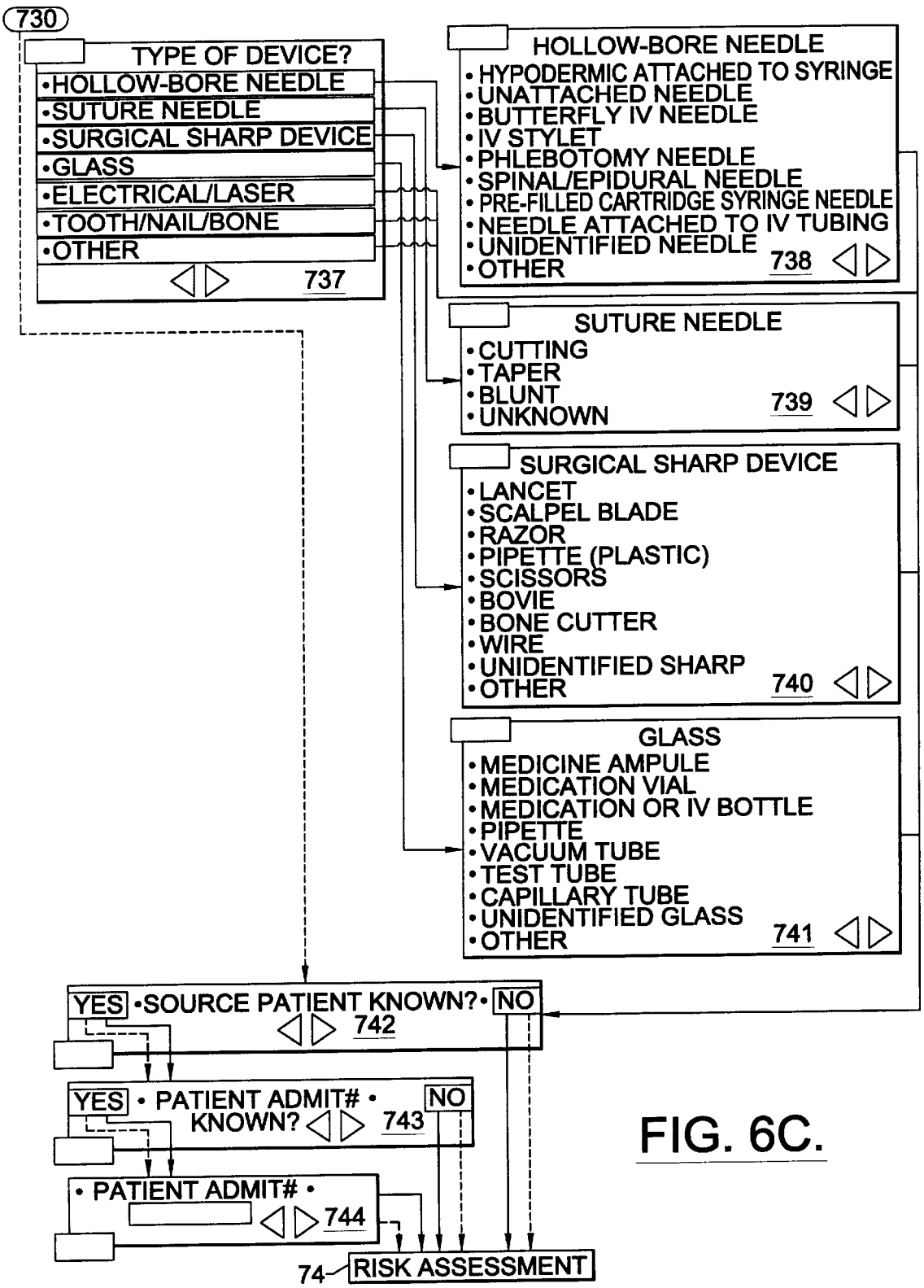
Figure 6D:
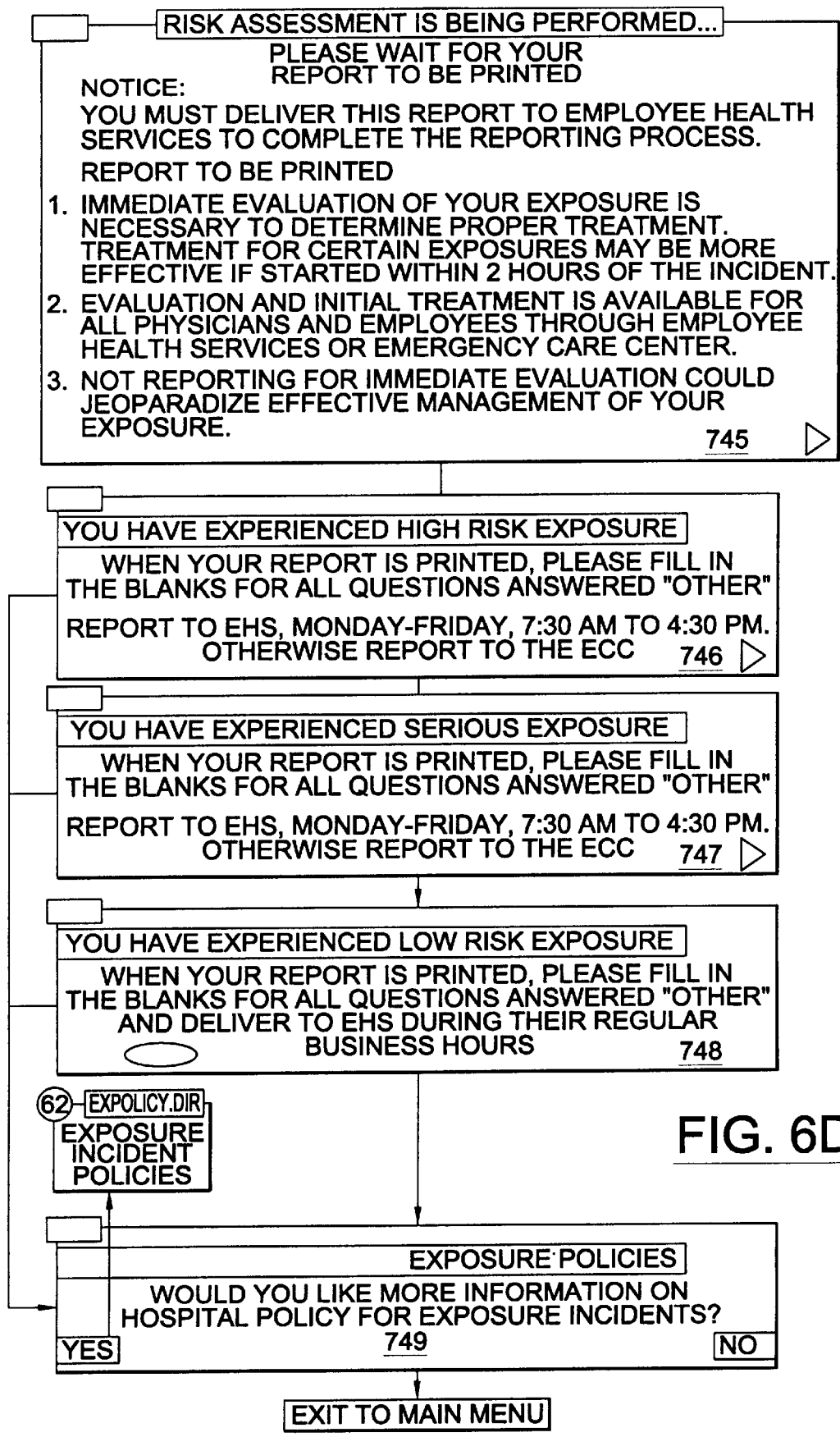

The exposure site is elicited (block 730), the answer to which leads to another series of queries (FIG. 6B). If the accident occurred in an emergency or operating room, the type of case is requested (block 731) and its length (block 732). For all accident locations, when the exposure occurred is requested (block 733) and how (blocks 734–736), and then the type of device involved (block 737).

Entering the type of device leads the user to more detailed queries (FIG. 6C) regarding each device type listed (blocks 738–741). The following series of queries is reached either upon entering data on the device details or if the exposure location query is bypassed (block 730). These queries relate to the source patient: if known (block 742), if admitting number known (block 743), and the admitting number (block 744).

Finally the risk assessment 74 is calculated (FIG. 6D), and the appropriate assessment displayed (blocks 746–748), along with instructions on how to proceed. The user is then led to a choice to view further information on exposure policies (block 749), a positive answer to which leads to the above-discussed information subsystem 62 (FIG. 3).

Returning to FIG. 2, following the risk evaluation 74 a report is printed 75 for the user.

The data collected are then routed 76 to the central processor 14, where they are held until uploading to the remote facility 50. It will clear be clear to one of skill in the art that the data collected can be of substantial utility, both for the local facility and the community at large. It is believed that use of the system 10 will significantly increase incident reporting, aid the user in a timely and confidential fashion, and permit the facility to amend or create procedures where data indicate improvements are warranted. On a larger scale, statistics gathered can aid in formulating procedures, in providing reengineered devices where warranted, and in tracking diseases.

It may be appreciated by one skilled in the art that additional embodiments may be contemplated that are not necessarily limited to the behavioral health care arena, including an analogous system and method for any medical or occupational/physical therapy information system.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. An interactive system for providing exposure and incident information to a healthcare worker comprising:

means for accessing an electronic database containing exposure and incident information; and display and input means in electronic communication with the access means for permitting a user to selectively view healthcare information on a desired topic and for entering data regarding an exposure or an incident into the database for collecting exposure and incident data at a healthcare facility;

wherein the database includes information comprising a set of procedures recommended following an exposure or incident, the access and display means located in close proximity to an area having a relatively high likelihood of exposures or incidents, for permitting the user ready access to the information.

2. The system recited in claim 1, wherein the access means comprises network means for electronically interfacing with a remote processor having the database resident thereon.

3. The system recited in claim 2, wherein the access means comprises a plurality of access means, each in network communication with a remote processor, and the display means comprises a plurality of display means, each display means in electronic communication with a corresponding access means.

4. The system recited in claim 1, wherein the access means further comprises means for interacting with an electronic testing means selectable with the use of the input means for permitting a user to obtain healthcare education in a selected subject area at a user-selected time and location.

5. The system recited in claim 4, wherein the interacting means further comprises means for permitting the user to obtain instruction on utilizing healthcare devices and technology.

6. The system recited in claim 1, further comprising means for outputting a copy of selected healthcare information from the access means in a form adapted for permitting the worker to carry the copy for subsequent review at another location.

7. An interactive system for providing exposure and incident information to a healthcare worker comprising:

means for accessing an electronic database containing exposure and incident information, including means for interacting with an electronic testing means;

display and input means in electronic communication with the access means for permitting a user to selectively view healthcare information on a desired topic and to obtain healthcare education in a selected subject area at a user-selected time and location;

wherein the database includes information comprising a set of procedures recommended following an exposure or incident, the access and display means located in close proximity to an area having a relatively high likelihood of exposures or incidents, for permitting the user ready access to the information; and wherein the interacting means further comprises means for utilizing electronic testing results calculated by the electronic testing means to grant certification upon the user achieving a satisfactory score.

8. An interactive system for providing timely exposure and incident information to a healthcare worker comprising:

a processor having an electronic database resident thereon containing exposure and incident information;

means in electronic communication with the processor for accessing a remote facility containing updated exposure and incident information and for downloading therefrom the updated exposure and incident information into the database;

means in electronic communication with the processor for accessing the database;

display and input means in electronic communication with the access means for permitting a user to selectively view healthcare information on a desired topic, the display and input means further comprising means for entering data relating to an incident or exposure; and the processor further having means resident thereon for calculating a risk assessment for the incident or exposure and for communicating the risk assessment to the user via the display means and for collecting data relating to the entered data relating to an incident or exposure.

9. The system recited in claim 8, wherein:

the database contains a plurality of recommended treatment and followup procedures, each correlated with a subset of the exposure and incident information; and the processor further has means resident thereon for correlating the risk assessment with a recommended treatment and followup procedure for the entered incident or exposure data and for communicating the recommended treatment and followup procedure to the user via the display means.

10. A portable interactive system for providing timely exposure and incident information to a healthcare worker at a remote facility comprising:

a portable processor having means for establishing electronic communication with a processor at a central facility, the central facility processor containing a database having updated exposure and incident information therein; and display and input means in electronic communication with the portable processor for permitting the healthcare worker to selectively view exposure and incident information on a desired topic, the display and input means comprising means for entering data relating to an incident or exposure; and the communication establishing means further comprising means for accessing software means resident on the central facility processor for calculating a risk assessment for the incident or exposure, for communicating the risk assessment to the user via the display means, and for collecting the entered data relating to the incident or exposure.

11. The system recited in claim 10, wherein the communication establishing means further comprises means for accessing a database resident in the central facility processor containing a plurality of recommended treatment and followup procedures, each correlated with a subset of the exposure and incident information, having means resident thereon for correlating the risk assessment with a recommended treatment and followup procedure for the entered incident or exposure data, and having means for communicating the recommended treatment and followup procedure to the user via the display means.

12. An interactive system for collecting exposure and incident data at a healthcare facility in a confidential manner, the system comprising:

input and display means; and a processor in electronic communication with the input means and the display means, the processor having resident thereon occupational safety software means having:

means for collecting data from a healthcare worker regarding an exposure or incident;

means for collating the data with previously collected data for amassing exposure and incident data for the facility; and means for assigning the worker a code for association with the collected data, for protecting the confidentiality of the worker.

13. The system recited in claim 12, wherein the data collecting means comprises means for posing a series of exposure and incident queries to a user via the display means, each subsequent query selected based upon an answer received from the input means to a prior query.

14. The system recited in claim 12, wherein the software means further has means for presenting on the display means a recommended procedure commensurate with the exposure and incident data input by the user.

15. The system recited in claim 12, wherein the software means further has means for rating the collated answers to calculate a relative risk assessment for the user.

16. The system recited in claim 12, further comprising means for linking the processor with a remote data collection facility and means for transferring the collected exposure and incident data to the remote data collection facility, for gathering multifacility data.

17. The system recited in claim 16, wherein the remote facility comprises a regulatory agency, and wherein the data transferring means comprises means for complying with reporting requirements of the regulatory agency.

18. An interactive information-providing and exposure and incident data collection system for healthcare facility workers comprising:

input means for receiving exposure and incident data from a healthcare worker;

output means; and a processor in electronic communication with the input and output means, the processor in electronic communication with a database containing exposure and incident information and procedures and with a software program adapted to relate the input exposure and incident data with correlated database information and procedures and to integrate the input exposure and incident data with the correlated database information, the processor having means for outputting the correlated database information and procedures to the healthcare worker via the output means.

19. The system recited in claim 18, wherein the input means and output means comprise a plurality of stations, each station including a terminal having a display and data entry means, each station networked to the processor.

20. The system recited in claim 19, wherein the display and data entry means and the output means comprise a touch-sensitive video monitor.

21. The system recited in claim 20, wherein the output means further comprises at least one device selected from the group consisting of a printer and a disk drive.

22. The system recited in claim 19, wherein the input means comprises at least one device selected from a group consisting of a keyboard, a pointing device, and a data storage device.

23. The system recited in claim 18, wherein the processor is further in communication with a second database containing safety education information, the input means further comprising means for accessing the second database, the processor further having means for outputting the safety information to the healthcare worker via the output means.

24. The system recited in claim 18, wherein the processor is further in communication with a third database containing product and technology information, the input means further comprising means for accessing the third database, the processor further having means for outputting the product and technology information to the healthcare worker via the output means.

25. The system recited in claim 18, wherein the processor is further in communication with an electronic testing means selectable with the use of the input means, for permitting a user to obtain healthcare education information in a selected subject area at a user-selected time and location.

26. An interactive information-providing and exposure and incident data collection system for healthcare facility workers comprising:

input means for receiving exposure and incident data from a healthcare worker;

output means; and a processor in electronic communication with the input and output means, the processor in electronic communication with a database containing exposure and incident information and procedures, with a software program adapted to relate the input exposure and incident data with correlated database information and procedures, and with an electronic testing means selectable with the use of the input means, for permitting a user to obtain healthcare education information in a selected subject area at a user-selected time and location, the processor having means for outputting the correlated database information and procedures and education information to the healthcare worker via the output means;

wherein the electronic testing means comprises evaluation means for calculating whether to grant certification based upon the user achieving a satisfactory score.

27. A method for providing exposure and incident information to a healthcare worker comprising the steps of:

providing a terminal in close proximity to an area within a healthcare facility having a relatively high likelihood of exposures or incidents;

accessing by means of the terminal an electronic database containing exposure and incident information;

accessing by means of the terminal an electronic testing software program;

administering a healthcare-related test to a healthcare worker via the terminal;

electronically scoring the test; and informing the worker via the terminal whether the worker passed the test.

28. The method recited in claim 27, further comprising the step of updating at predetermined intervals the electronic database via a download from a remote processor.

29. The method recited in claim 27, further comprising the steps of:
   entering exposure and incident information into a processor via the terminal;
   correlating the exposure and incident information with the electronic database to extract a relevant subset thereof;
   displaying to the worker the relevant subset.

30. The method recited in claim 29, wherein the relevant subset comprises a recommended treatment and followup procedure.

31. The method recited in claim 29, further comprising the step of calculating a risk assessment based upon the entered exposure and incident information.

32. A method for reducing risk from incidents and exposures within a healthcare facility comprising the steps of:
   providing a terminal in close proximity to an area within a healthcare facility having a relatively high likelihood of exposures or incidents;
   entering exposure and incident information into a processor via the terminal;
   creating an electronic database of entered exposure and incident information for the facility; and
   analyzing the database to determine a frequency distribution of each of a set of exposure and incident types to identify a particular type for which remedial action is recommended.

33. A method for improving compliance with safety regulations regarding incidents and exposures within a healthcare facility comprising the steps of:
   providing a terminal in close proximity to an area within a healthcare facility having a relatively high likelihood of exposures or incidents;
   entering exposure and incident information into a processor via the terminal;
   uploading at least a portion of the entered exposure and incident information for the facility to a regulatory agency, the portion uploaded for compliance with reporting requirements of the agency.

* * * * *